United States Patent [19]

Hawking et al.

[11] 3,995,024

[45] Nov. 30, 1976

[54] DENTIFRICE

[75] Inventors: Brian Rae Hawking; Kenneth William Hetherington, both of Twickenham, England

[73] Assignee: Beecham Group Limited, Brentford, England

[22] Filed: Mar. 20, 1975

[21] Appl. No.: 560,196

[30] Foreign Application Priority Data

Apr. 26, 1974 United Kingdom............... 18357/74

[52] U.S. Cl. ................................................. 424/55
[51] Int. Cl.² ........................................... A61K 7/16
[58] Field of Search ................. 424/49, 50, 51, 52, 424/53, 54, 55

[56] References Cited

UNITED STATES PATENTS 2,839,448   6/1958   Hager et al. .......................... 424/49

OTHER PUBLICATIONS

Gubner et al., "*Dental Therapeutic Comp.*" Can. 680,168, Feb. 2, 1964, pp. 265–280.

*Primary Examiner*—Lewis Gotts
*Assistant Examiner*—Cary Owens

[57] ABSTRACT

Dentifrice compositions containing a water-soluble anionic cellulose derivative and stable against syneresis due to its content of a water-soluble salt of a hydroxybenzoate ester and a water-swellable clay of natural or synthetic origin. The salt is preferably a sodium lower alkyl p-hydroxybenzoate.

9 Claims, No Drawings

DENTIFRICE

This invention relates to a dentifrice and in particular to a dentifrice with a reduced tendency to lose rigidity and viscosity.

In order to prevent separation of the ingredients of a toothpaste on storage it is necessary to incorporate a binding agent, or thickener. Thickeners used in dentifrices are hydrophilic colloids which disperse in aqueous media. The most commonly used thickeners are cellulose derivatives because these are cheap and their quality can be closely controlled. Examples include sodium carboxymethyl cellulose and cellulose ethers such as methyl cellulose, hydroxy-ethyl and hydroxy-propyl cellulose. Occasionally however, dentifrices incorporating cellulose thickeners are subject to syneresis, i.e. severe loss of rigidity and viscosity, apparently due to the action of cellulytic enzymes, which can be produced by micro-organisms present in some batches of the cellulose thickener.

We have now found that a dentifrice composition containing a water-soluble anionic cellulose derivative is stabilised against syneresis by incorporating a water-soluble salt of a hydroxybenzoate ester together with a water-swellable clay of natural or synthetic origin. Hydroxy benzoate esters are known as anti-bacterial materials, but we have surprisingly found that they (and the swelling clays) have anti-enzyme activity. The combination of the two groups of materials is more effective than either when used alone.

Accordingly the present invention provides a dentifrice comprising a water-soluble anionic cellulose derivative as thickening agent; a natural or synthetic water swellable clay; and a water soluble salt of a hydroxybenzoic acid ester having 1 to 7 carbon atoms in the ester portion.

The invention is applicable to a dentifrice formulation which includes any water soluble anionic derivative of cellulose present as a thickening agent, provided the latter is compatible with the other constituents of the composition, particularly sodium carboxymethyl cellulose. The dentifrice formulation should not contain any substances which precipitate the hydroxybenzoic acid ester salt from solution.

The clay may be of natural mineral origin, for example china clay, kaolin, fuller's earth, Bentonite (a colloidal clay derived from volcanic ash) or Veegum (Trade Mark) (a processed magnesium aluminium silicate); or alternatively the clay may be synthetic, such as an inorganic silica clay, for example Laponite (Trade Mark). Many such clays are employed in dentifrice compositions as gelling agents and are characterised by their ability to swell in water.

Hydroxybenzoate ester salts are used in this invention in conjunction with the clay. Preferably p-hydroxybenzoic acid ester salts are used and suitable esters are $C_{1-7}$ alkyl esters such as methyl, ethyl, n-and iso-propyl, and n-. sec- and tert-butyl esters. The salt is water soluble, especially alkali metal or ammonium salts. Typical examples of individual compounds which may be employed include sodium methyl p-hydroxy benzoate; and sodium propyl p-hydroxy benzoate.

Suitably the toothpaste of this invention comprises from 0.1 – 1.0%, preferably from 0.1 – 0.4% by weight of the clay and from 0.05 – 0.5%, preferably from 0.05 – 0.15% by weight of the benzoate ester salt.

The dentifrices of this invention are preferably in the form of toothpastes. A toothpaste will usually also comprise an abrasive material, a detergent, humectant, flavouring agent, preservative and colour. Typical toothpaste abrasives include calcium carbonate, calcium phosphates such as dicalcium phosphate, anhydrous or dihydrate, tricalcium phosphate, calcium pyrophosphate, insoluble sodium metaphosphate, magnesium phosphates, magnesium carbonate, various types of alumina and silica, various silicates such as magnesium and aluminiumsilicate and polymers such as polystyrene, polymethylmethacrylate, polyamines, polycarbonates, polyesters, ureaformaldehyde resins, melamine - formaldehyde resins and phenol-formaldehyde resins.

Commonly-used dental detergents include sodium lauryl sulphate, sodium N-lauroyl sarcosinate and ricinoleate and sulphoricinoleate derivatives.

Suitable humectants include glycerol and sorbitol and also other polyalcohols such as propanediol and/or butanediol.

The dentifrice may also contain the conventional flavouring and sweetening substances such as peppermint or spearmint oil, menthol, chloroform, or oil of clove, wintergreen, eucalyptus, aniseed, rose, lavender; saccharin and sodium cyclamate.

Examples of preservatives which may be incorporated into the dentifrice, in addition to p-hydroxybenzoate esters include hexachloraphen; and known surfactants.

If desired colour may also be imparted to the dentifrice by means of dyestuffs; or bleaches; or optical brighteners may be incorporated, such as sodium perborate, magnesium peroxide, hydrogen peroxide-urea compounds.

This invention is illustrated by the following Examples of toothpaste formulations. The formulations listed in Examples 1 to 4 are remarkably stable even when containing added cellulose enzyme. Similar formulations to those of Examples 1 to 4 except that hydroxybenzoate ester salts and swelling clay are omitted are unstable. Similar formulations containing only hydroxybenzoate ester salts or only swelling clays are only slightly more stable than formulations containing neither.

EXAMPLE 1

| | % w/w |
|---|---|
| Glycerin | 25.00 |
| Sodium carboxymethyl cellulose | 0.8 |
| Laponite (5% solution) | 6.0 |
| Sodium methyl p-hydroxybenzoate | 0.1 |
| Calcium carbonate | 50.0 |
| Sodium Lauryl sulphate | 1.5 |
| Flavour | q.s. |
| Water | to 100.0 |

EXAMPLE 2

| | % w/w |
|---|---|
| Glycerin | 25.00 |
| Sodium carboxymethyl cellulose | 0.80 |
| Veegum | 0.10 |
| Sodium Salts of unidentified mixed esters of p-hydroxy- | |

-continued

EXAMPLE 2

| | |
|---|---|
| benzoic acid ("Nipasept Na" ex Nipa Laboratories, Treforest Trading Estate, Pontypridd, Glamorgan, Wales) | 0.10 |
| Hydrated Alumina | 50.0 |
| Sodium Lauryl Sulphate | 1.5 |
| Flavour | q.s. |
| Water | to 100.0 |

EXAMPLE 3

| | % w/w |
|---|---|
| Glycerin | 12.50 |
| 70% Sorbitol Solution | 12.50 |
| Sodium carboxymethyl-cellulose | 1.00 |
| Laponite (5% solution) | 6.00 |
| Calcium carbonate | 50.0 |
| Sodium lauryl sulphate | 1.5 |
| Flavour | q.s. |
| Water | to 100.0 |

EXAMPLE 4

| | % w/w |
|---|---|
| Glycerin | 25.00 |
| Sodium carboxymethyl-cellulose | 0.80 |
| Veegum | 0.10 |
| Sodium methyl p-hydroxy-benzoate | 0.10 |
| Insoluble sodium meta phosphate | 45.00 |
| Sodium lauryl sulphate | 1.50 |
| Flavour | q.s. |
| Water | to 100.0 |

We claim:
1. A method of stabilizing against syneresis dentifrice compositions containing a compatible water-soluble anionic cellulose derivative as thickening agent, which comprises including in the dentifrice composition a natural or synthetic water-swellable clay as gelling agent and a water-soluble salt of a hydroxybenzoic acid ester having 1 to 7 carbon atoms in the ester portion in a combined amount sufficient to stabilize the dentifrice composition against syneresis.

2. A method as claimed in claim 1 wherein the cellulose derivative is sodium carboxymethyl cellulose.

3. A method as claimed in claim 1 wherein the hydroxybenzoic acid ester salt is a p-hydroxybenzoic acid ester salt.

4. A method as claimed in claim 3 wherein the hydroxybenzoic acid ester salt contains a methyl p-hydroxybenzoate salt.

5. A method as claimed in claim 1 wherein the hydroxybenzoic acid ester salt is a sodium salt.

6. A dentifrice composition containing a compatible water-soluble anionic cellulose derivative as thickening agent and stable against syneresis, said composition having incorporated therein a water-soluble salt of a hydroxybenzoate ester having 1 to 7 carbon atoms in the ester part and a water-swellable clay as gelling agent in a combined amount sufficient to stabilize the dentifrice against syneresis.

7. A dentifrice composition according to claim 6 wherein the anionic cellulose derivative is sodium carboxymethylcellulose.

8. A dentifrice composition according to claim 7 wherein the hydroxybenzoate ester salt amounts to 0.05–0.50% and the clay amounts to 0.1–1.0%, by weight.

9. A dentifrice composition according to claim 7 wherein the hydroxybenzoate ester salt amounts to 0.05–0.15% and the clay amounts to 0.1–0.4%, by weight.

* * * * *